US010045137B2

(12) United States Patent
Skoglund et al.

(10) Patent No.: US 10,045,137 B2
(45) Date of Patent: Aug. 7, 2018

(54) BI-MAGNITUDE PROCESSING FRAMEWORK FOR NONLINEAR ECHO CANCELLATION IN MOBILE DEVICES

(71) Applicant: Google Inc., Mountain View, CA (US)

(72) Inventors: Jan Skoglund, San Francisco, CA (US); Yiteng Huang, Bridgewater, NJ (US); Alejandro Luebs, Mountain View, CA (US)

(73) Assignee: Google LLC, Mountain View, CA (US)

( * ) Notice: Subject to any disclaimer, the term of this patent is extended or adjusted under 35 U.S.C. 154(b) by 0 days.

(21) Appl. No.: 15/639,263

(22) Filed: Jun. 30, 2017

(65) Prior Publication Data

US 2018/0007482 A1   Jan. 4, 2018

Related U.S. Application Data

(60) Provisional application No. 62/356,766, filed on Jun. 30, 2016.

(51) Int. Cl.
*H04R 29/00* (2006.01)
*H04B 3/23* (2006.01)
(Continued)

(52) U.S. Cl.
CPC ....... *H04R 29/001* (2013.01); *G01N 29/4427* (2013.01); *H04B 3/237* (2013.01); *G10L 2021/02082* (2013.01)

(58) Field of Classification Search
CPC .................................................... H04R 29/00
See application file for complete search history.

(56) References Cited

U.S. PATENT DOCUMENTS

2007/0206777 A1\* 9/2007 Fadili ................... H04M 9/082
  379/406.01
2009/0147942 A1\* 6/2009 Culter ................... H04M 9/082
  379/406.06

(Continued)

FOREIGN PATENT DOCUMENTS

CN          102118530 A          7/2011

OTHER PUBLICATIONS

"Dynamic range compression", Wikipedia, The Free Encyclopedia, https://en.wikipedia.org/wiki/Dynamic_range_compression, 2016, 10 pages.

(Continued)

*Primary Examiner* — Olisa Anwah
(74) *Attorney, Agent, or Firm* — Brake Hughes Bellermann LLP (57) ABSTRACT

Techniques of performing acoustic echo cancellation involve providing a bi-magnitude filtering operation that performs a first filtering operation when a magnitude of an incoming audio signal to be output from a loudspeaker is less than a specified threshold and a second filtering operation when the magnitude of the incoming audio signal is greater than the threshold. The first filtering operation may take the form of a convolution between the incoming audio signal and a first impulse response function. The second filtering operation may take the form of a convolution between a nonlinear function of the incoming audio signal and a second impulse response function. For such a convolution, the bi-magnitude filtering operation involves providing, as the incoming audio signal, samples of the incoming audio signal over a specified window of time. The first and second impulse response functions may be determined from an input signal input into a microphone.

20 Claims, 4 Drawing Sheets

(51) Int. Cl.
*G01N 29/44* (2006.01)
*G10L 21/0208* (2013.01)

(56) References Cited

U.S. PATENT DOCUMENTS

| | | | | |
|---|---|---|---|---|
| 2014/0169568 A1* | 6/2014 | Li | H04M 9/082 | 381/17 |
| 2014/0177859 A1* | 6/2014 | Ahgren | H04R 3/002 | 381/71.1 |
| 2015/0133097 A1* | 5/2015 | Jang | H04M 3/568 | 455/416 |
| 2015/0187348 A1* | 7/2015 | Kang | G10L 21/0208 | 381/66 |
| 2016/0094718 A1* | 3/2016 | Mani | H04M 9/082 | 379/406.12 |
| 2016/0127827 A1* | 5/2016 | Tzirkel-Hancock | H04R 3/002 | 381/71.4 |
| 2017/0142532 A1* | 5/2017 | Pan | H04R 29/001 | |
| 2017/0171380 A1* | 6/2017 | Singh | H04M 3/002 | |
| 2017/0208170 A1* | 7/2017 | Mani | H04M 3/002 | |
| 2017/0295283 A1* | 10/2017 | Mani | H04M 1/20 | |
| 2017/0330579 A1* | 11/2017 | Zhang | G10L 21/0205 | |

OTHER PUBLICATIONS

"Gain stage", Wikipedia, The Free Encyclopedia, https://en.wikipedia.org/wiki/Gain_stage, 2015, 1 page.

"WebRTC", Wikipedia, The Free Encyclopedia, https://en.wikipedia.org/wiki/WebRTC, 2016, 4 pages.

Bendersky, et al., "Nonlinear residual acoustic echo suppression for high levels of harmonic distortion", Proc. IEEE ICASSP, 2008, pp. 261-264.

Breining, et al., "Acoustic echo control—an application of very-high-order adaptive filters", IEEE Signal Process. Mag., vol. 16, No. 4, Jul. 1999, pp. 42-69.

Enzner, "Acoustic echo control", Academic Press Library in Signal Processing, R. Chellappa and S. Theodoridis, Eds., chapter 30, Elsevier Academic Press, Chennai, India, 2014, pp. 807-878.

Gil-Cacho, et al., "Nonlinear acoustic echo cancellation based on a parallel-cascade kernel affine projection algorithm", Proc. IEEE ICASSP, vol. 1, 2012, pp. 33-36.

Google Inc., "AppRTC Demo Code", https://github.com/webrtc/apprtc, 2016, 4 pages.

Google Inc., "AppRTC", https://appr.tc, 2016, 1 page.

Ikram, "Non-linear acoustic echo cancellation using cascaded Kalman filtering", Proc. IEEE ICASSP, 2014, pp. 1320-1324.

Klippel, "Dynamic measurement and interpretation of the nonlinear parameters of electrodynamic loudspeakers", J. Audio Eng. Soc., vol. 38, No. 12, Dec. 1990, pp. 944-955.

Kuech, et al., "Nonlinear acoustic echo cancellation using adaptive orthogonalized power filters", Proc. IEEE ICASSP, vol. 3, 2005, pp. 105-108.

Kuech, "Nonlinear residual echo suppression using a power filter model of the acoustic echo path", Proc. IEEE ICASSP, vol. 1, 2007, pp. 73-76.

Lewis, "Understanding microphone sensitivity", Analog Dialogue 46-05 Back Burner, May 2012, 3 pages.

Malik, et al., "A variational bayesian learning approach for nonlinear acoustic echo control", IEEE Trans. Signal Process., vol. 61, No. 23, Dec. 2013, pp. 5853-5867.

Mossi, et al., "An assessment of linear adaptive filter performance with nonlinear distortions", Proc. IEEE ICASSP, 2010, pp. 313-316.

Mossi, et al., "Robust and low-cost cascaded non-linear acoustic echo cancellation", Proc. IEEE ICASSP, 2011, pp. 89-92.

Nollett, et al., "Nonlinear echo cancellation for hands-free speakerphones", Proc. NSIP, 1997, 5 pages.

International Search Report and Written Opinion for PCT Application No. PCT/US2017/040313, dated Sep. 11, 2017, 12 Pages.

Shi, et al., "A channel shortening approach for nonlinear acoustic echo cancellation", Proc. IEEE Workshop on Statistical Signal Processing, 2007, pp. 351-354.

Stenger, et al., "Adaptation of a memoryless preprocessor for nonlinear acoustic echo cancelling", Signal Processing (Elsevier), vol. 80, No. 9, Sep. 2000, pp. 1747-1760.

Stenger, et al., "Nonlinear acoustic echo cancellation with 2nd order adaptive Volterra filters", Proc. IEEE ICASSP, vol. 2, Mar. 1999, pp. 877-880.

* cited by examiner

BI-MAGNITUDE PROCESSING FRAMEWORK FOR NONLINEAR ECHO CANCELLATION IN MOBILE DEVICES

CROSS REFERENCE TO RELATED APPLICATION

This application claims priority to U.S. Provisional Application No. 62/356,766, filed on Jun. 30, 2016, the disclosure of which is incorporated herein by reference in its entirety.

TECHNICAL FIELD

This description relates to acoustic echo cancellation in mobile devices.

BACKGROUND

In some voice communication systems, acoustic echo occurs when a loudspeaker and a microphone become coupled. An example of such a voice communication system is Web Real-Time Communication (WebRTC), which is a web-browser enabled communications system. Such web-browser enabled communications systems offer software-based acoustic echo cancellation (AEC) operation to reduce or eliminate acoustic echo. A conventional AEC operation includes using an adaptive filter to identify an echo path of an echo in audio output from the loudspeaker, synthesizing a replica of the echo, and subtracting the replica of the echo from an audio input into the microphone.

SUMMARY

In one general aspect, a method can include receiving, by processing circuitry configured to reduce acoustic echo in an audio system including a loudspeaker and a microphone, at the loudspeaker of the audio system, an audio signal from a source location remote from the audio system. The method can also include performing, by the processing circuitry, a comparison operation on a magnitude of the audio signal and a threshold magnitude to produce a comparison result. The method can further include, in response to the comparison result indicating that the magnitude of the audio signal is less than the threshold magnitude, performing, by the processing circuitry, a first filtering operation on an input signal input into the microphone of the audio system to produce a first filtered input signal; and transmitting, by the processing circuitry, the first filtered input signal to the source location. The method can further include, in response to the comparison result indicating that the magnitude of the audio signal is greater than the threshold magnitude, performing, by the processing circuitry, a second filtering operation on an input signal input into the microphone of the audio system to produce a second filtered input signal, the second filtered input signal being distinct from the first filtered input signal; and transmitting, by the processing circuitry, the second filtered input signal to the source location.

The details of one or more implementations are set forth in the accompanying drawings and the description below. Other features will be apparent from the description and drawings, and from the claims.

DETAILED DESCRIPTION

The above-described conventional acoustic echo cancellation (AEC) operation assumes that the echo path is linear. While this assumption is true for audio systems connected to desktop and laptop computers, it is not true for mobile devices which have low-quality audio components whose inputs and outputs are very close together. For mobile devices, the echo path may be nonlinear. In this case, the conventional AEC operation may be ineffective in removing echo from the audio input.

In accordance with the implementations described herein and in contrast with the above-described conventional AEC operation, improved techniques of performing AEC operations involve providing a bi-magnitude filtering operation that performs a first filtering operation when a magnitude of an incoming audio signal to be output from a loudspeaker is less than a specified threshold and a second filtering operation when the magnitude of the incoming audio signal is greater than the threshold. For example, the first filtering operation may take the form of a convolution between the incoming audio signal and a first impulse response function. In one example, the first impulse response function can be a generic impulse response function that optimizes a power of a residual signal, e.g., minimizing the power of the residual signal. In this example, the second filtering operation may take the form of a convolution between a nonlinear function of the incoming audio signal and a second impulse response function. For such a convolution, the bi-magnitude filtering operation involves providing, as the incoming audio signal, samples of the incoming audio signal over a specified window of time. The first and second impulse response functions may be determined from an input signal input into a microphone. In some implementations, each of the impulse response functions is computed from a minimization of a power of a residual between the input signal and the respective output of the convolution.

Advantageously, the above-described magnitude dependent switch between the first and second filtering operations provides a simple framework with which to treat nonlinear echo paths in software-based communication systems in mobile devices.

Figure 1:
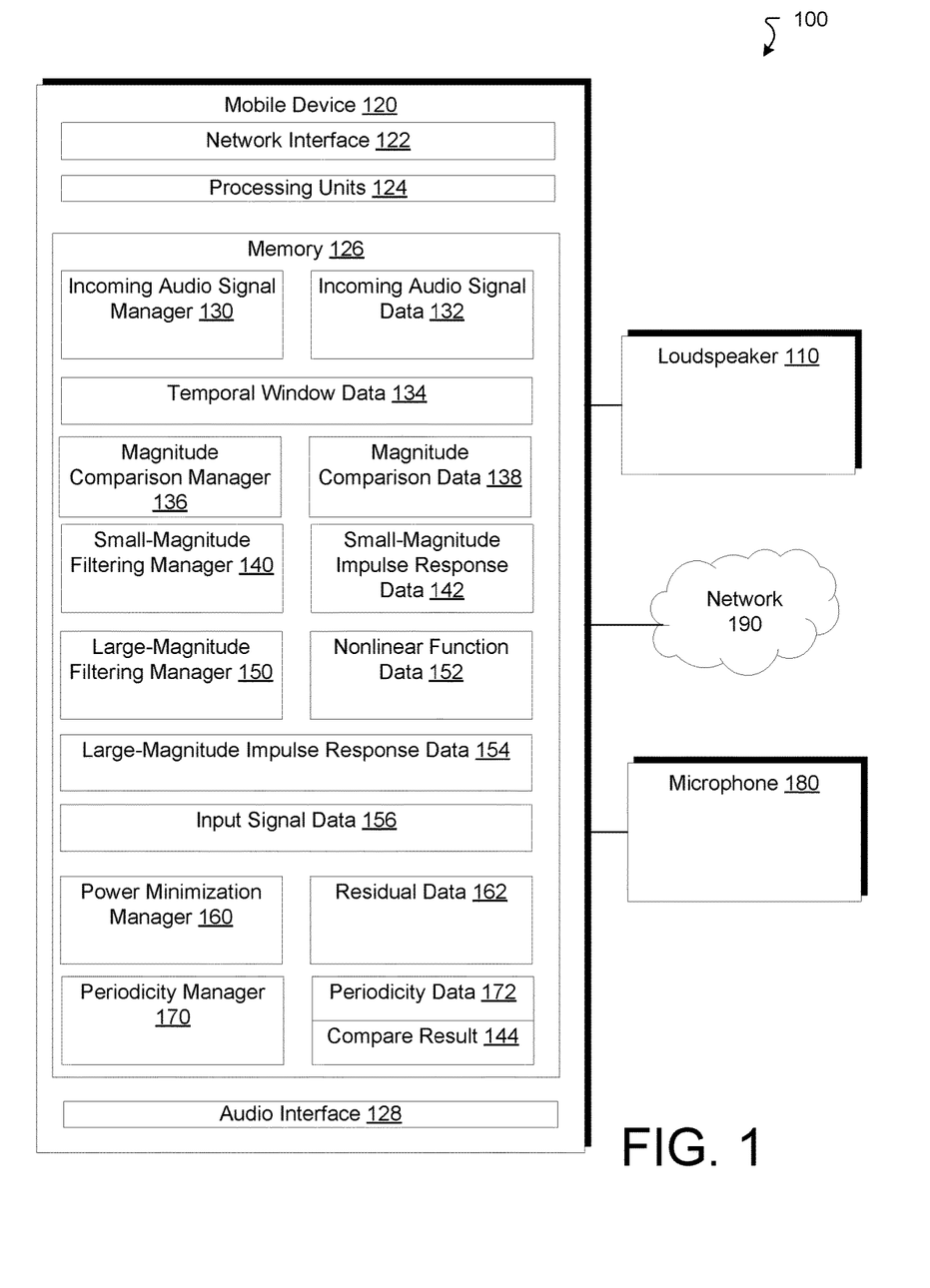
FIG. 1 is a diagram that illustrates an example electronic environment for implementing improved techniques described herein.

FIG. 1 is a diagram that illustrates an example electronic environment 100 in which the above-described improved techniques may be implemented. As shown, in FIG. 1, the example electronic environment 100 includes a mobile device 120 and a network 190. In some implementations, the mobile device 120 takes the form of a smartphone, a tablet computer, or the like.

The mobile device 120 is configured to provide acoustic echo cancellation. The mobile device 120 includes a loudspeaker 110, a network interface 122, one or more processing units 124, memory 126, an audio interface 128, and a microphone 180. The network interface 122 includes, for example, Ethernet adaptors, Token Ring adaptors, and the like, for converting electronic and/or optical signals received from the network 170 to electronic form for use by the point cloud compression computer 120. The set of processing units 124 include one or more processing chips and/or assemblies. The memory 126 includes both volatile memory (e.g., RAM) and non-volatile memory, such as one or more ROMs, disk drives, solid state drives, and the like. The set of processing units 124 and the memory 126 together form control circuitry, which is configured and arranged to carry out various methods and functions as described herein.

In some embodiments, one or more of the components of the mobile device 120 can be, or can include processors (e.g., processing units 124) configured to process instructions stored in the memory 126. Examples of such instructions as depicted in FIG. 1 include an incoming audio signal manager 130, a magnitude comparison manager 136, a small-magnitude filtering manager 140, a large-magnitude filtering manager 150, a power minimization manager 160, and a periodicity manager 170. Further, as illustrated in FIG. 1, the memory 126 is configured to store various data, which is described with respect to the respective managers that use such data.

The incoming audio signal manager 130 is configured to receive incoming audio signal data 132 over the network interface 122 from an audio source remote from the mobile device 120, e.g., a party at a far end of a WebRTC session. The incoming audio signal manager 130, in receiving the audio signal data, is configured to sample an audio signal received over the network 190 at some frequency, e.g., 200 samples per second or more or less. Further, the incoming audio signal manager 130 is configured to store the resulting samples of the audio signal over a specified window of time specified in the temporal window data 134. The storing of the audio signal over such a window of time produces, as the incoming audio signal data 132, a windowed audio signal. In some implementations, the window of time 134 is specified as a fixed time, e.g., 200 milliseconds, or more or less. In some implementations, the window of time 134 is specified as a fixed number of samples, e.g., 40 samples per window, or more or less. In some implementations, the incoming audio signal manager 130 updates the windowed audio signal at a specified frequency, e.g., once per 200 milliseconds, or more or less frequently.

The magnitude comparison manager 134 is configured to compare a magnitude of the windowed audio signal 132 to a threshold magnitude specified in the magnitude comparison data 138 to produce a comparison result 144. The magnitude comparison manager 134 is also configured to select one of the small-magnitude filtering manager 140 or the large-magnitude filtering manager 150 for performing a filtering operation on the windowed audio signal 132 according to the comparison result 144. For example, if the comparison result 144 indicates that the magnitude is less than the threshold 138, then the magnitude comparison manager 134 is configured to select the small-magnitude filtering manager 140. In this example, if the comparison result 144 indicates that the magnitude is greater than the threshold 138, then the magnitude comparison manager 134 is configured to select the large-magnitude filtering manager 150.

In some implementations, the magnitude comparison manager 134 is configured to generate, as the magnitude of the windowed audio signal 132, the maximum of the absolute values of the amplitudes of the samples of the windowed audio signal 132 (i.e., the $L^\infty$ norm). In some implementations, the magnitude comparison manager 134 is configured to generate, as the magnitude of the windowed audio signal 132, the sum of the squares of the amplitudes of the samples of the windowed audio signal 132 (i.e., the $L^2$ norm).

The small-magnitude filtering manager 140 is configured to perform a convolution operation on the windowed audio signal 132 with the small-magnitude impulse response data 142. In some implementations, the number of samples of the small-magnitude impulse response data 142 is equal to the number of samples of the windowed audio signal 132. In some implementations, the number of samples of the small-magnitude impulse response data 142 is not equal to the number of samples of the windowed audio signal 132. In such an implementation, the small-magnitude filtering manager 140 is configured to use the minimum number of samples from the windowed audio signal 132 and the small-magnitude impulse response data 142.

The large-magnitude filtering manager 150 is configured to perform a convolution operation on a nonlinear function of the windowed audio signal 132 with the large-magnitude impulse response data 154. In some implementations, the number of samples of the large-magnitude impulse response data 154 is equal to the number of samples of the windowed audio signal 132. In some implementations, the number of samples of the large-magnitude impulse response data 154 is not equal to the number of samples of the windowed audio signal 132. In such an implementation, the large-magnitude filtering manager 150 is configured to use the minimum number of samples from the windowed audio signal 132 and the large-magnitude impulse response data 150.

Further, the large-magnitude filtering manager 150 is configured to perform a nonlinear function evaluation on each of the samples of the windowed audio signal 132 according to nonlinear function data 152. The nonlinear function data 152 specifies the nonlinear function evaluation to be performed by the large-magnitude filtering manager 150 in response to the comparison result 144 indicating that the magnitude is greater than the threshold 138. For example, the nonlinear function data 152 may indicate such a nonlinear function via a numerical indicator, a textual descriptor. The large-magnitude filtering manager 150 is configured to interpret such an indicator or descriptor and perform the nonlinear function evaluation according to that interpretation. In some implementations, the nonlinear function specified in the nonlinear function data 152 may take the form of a power of the value of a sample of the windowed audio signal 132, e.g., a square of the sample. In some implementations, such a nonlinear function may take the form of an absolute value, a square of the absolute value, or any power of the absolute value of a sample.

The power minimization manager 160 is configured to produce either the small-magnitude impulse response data 142 or the large-magnitude impulse response data 154 based on input signal data 156 received from the microphone 180 over the audio interface 128. In some implementations, the power minimization manager 160 is configured to form a residual as a difference between the input signal data 156 and a convolution output. The convolution output is a linear combination of unknown weights and the windowed audio signal 132. The power minimization manager 160 is then configured to determine either the small-magnitude impulse response data 142 or the large-magnitude impulse response data 154 by performing a minimization operation on the power, or the sum of the squares of the values of the samples of the unknown residual signal, over the unknown weights. The weights that the power minimization manager 160 determines from the minimization operation produce either the small-magnitude impulse response data 142 or the large-magnitude impulse response data 154 and the residual data 162. In some implementations, the power minimization manager 160 is configured to perform the minimization operation on the absolute value of the unknown residual, or a power of the absolute value of the unknown residual, to produce the weights.

The periodicity manager 170 is configured to cause the power minimization manager 160 to update the small-magnitude impulse response data 142 or the large-magnitude impulse response data 154 periodically according to a period specified in periodicity data 172. The period specified in the periodicity data 172 can be expressed in terms of absolute time intervals, e.g., 1 second, or more or less, or in terms of a number of windows of time, e.g., 1 or more windows of time.

The network 190 is configured and arranged to provide network connections between the mobile device 120 and any remote audio sources. The network 190 may implement any of a variety of protocols and topologies that are in common use for communication over the Internet or other networks. Further, the network 190 may include various components (e.g., cables, switches/routers, gateways/bridges, etc.) that are used in such communications.

In some implementations, the memory 126 can be any type of memory such as a random-access memory, a disk drive memory, flash memory, and/or so forth. In some implementations, the memory 126 can be implemented as more than one memory component (e.g., more than one RAM component or disk drive memory) associated with the components of the user device 120. In some implementations, the memory 126 can be a database memory. In some implementations, the memory 126 can be, or can include, a non-local memory. For example, the memory 126 can be, or can include, a memory shared by multiple devices (not shown). In some implementations, the memory 126 can be associated with a server device (not shown) within a network and configured to serve the components of the user device 120.

The components (e.g., modules, processing units 124) of the mobile device 120 can be configured to operate based on one or more platforms (e.g., one or more similar or different platforms) that can include one or more types of hardware, software, firmware, operating systems, runtime libraries, and/or so forth. In some implementations, the components of the mobile device 120 can be configured to operate within a cluster of devices (e.g., a server farm). In such an implementation, the functionality and processing of the components of the mobile device 120 can be distributed to several devices of the cluster of devices.

The components of the mobile device 120 can be, or can include, any type of hardware and/or software configured to process attributes. In some implementations, one or more portions of the components shown in the components of the mobile device 120 in FIG. 1 can be, or can include, a hardware-based module (e.g., a digital signal processor (DSP), a field programmable gate array (FPGA), a memory), a firmware module, and/or a software-based module (e.g., a module of computer code, a set of computer-readable instructions that can be executed at a computer). For example, in some implementations, one or more portions of the components of the mobile device 120 can be, or can include, a software module configured for execution by at least one processor (not shown). In some implementations, the functionality of the components can be included in different modules and/or different components than those shown in FIG. 1.

Although not shown, in some implementations, the components of the mobile device 120 (or portions thereof) can be configured to operate within, for example, a data center (e.g., a cloud computing environment), a computer system, one or more server/host devices, and/or so forth. In some implementations, the components of the mobile device 120 (or portions thereof) can be configured to operate within a network. Thus, the components of the mobile device 120 (or portions thereof) can be configured to function within various types of network environments that can include one or more devices and/or one or more server devices. For example, the network can be, or can include, a local area network (LAN), a wide area network (WAN), and/or so forth. The network can be, or can include, a wireless network and/or wireless network implemented using, for example, gateway devices, bridges, switches, and/or so forth. The network can include one or more segments and/or can have portions based on various protocols such as Internet Protocol (IP) and/or a proprietary protocol. The network can include at least a portion of the Internet.

In some embodiments, one or more of the components of the mobile device 120 can be, or can include, processors configured to process instructions stored in a memory. For example, the incoming audio signal manager 130 (and/or a portion thereof), the magnitude comparison manager 136 (and/or a portion thereof), the small-magnitude filtering manager 140 (and/or a portion thereof), the large-magnitude filtering manager 150 (and/or a portion thereof), the power minimization manager 160 (and/or a portion thereof), and the periodicity manager 170 (and/or a portion thereof) can be a combination of a processor and a memory configured to execute instructions related to a process to implement one or more functions.

Figure 2:
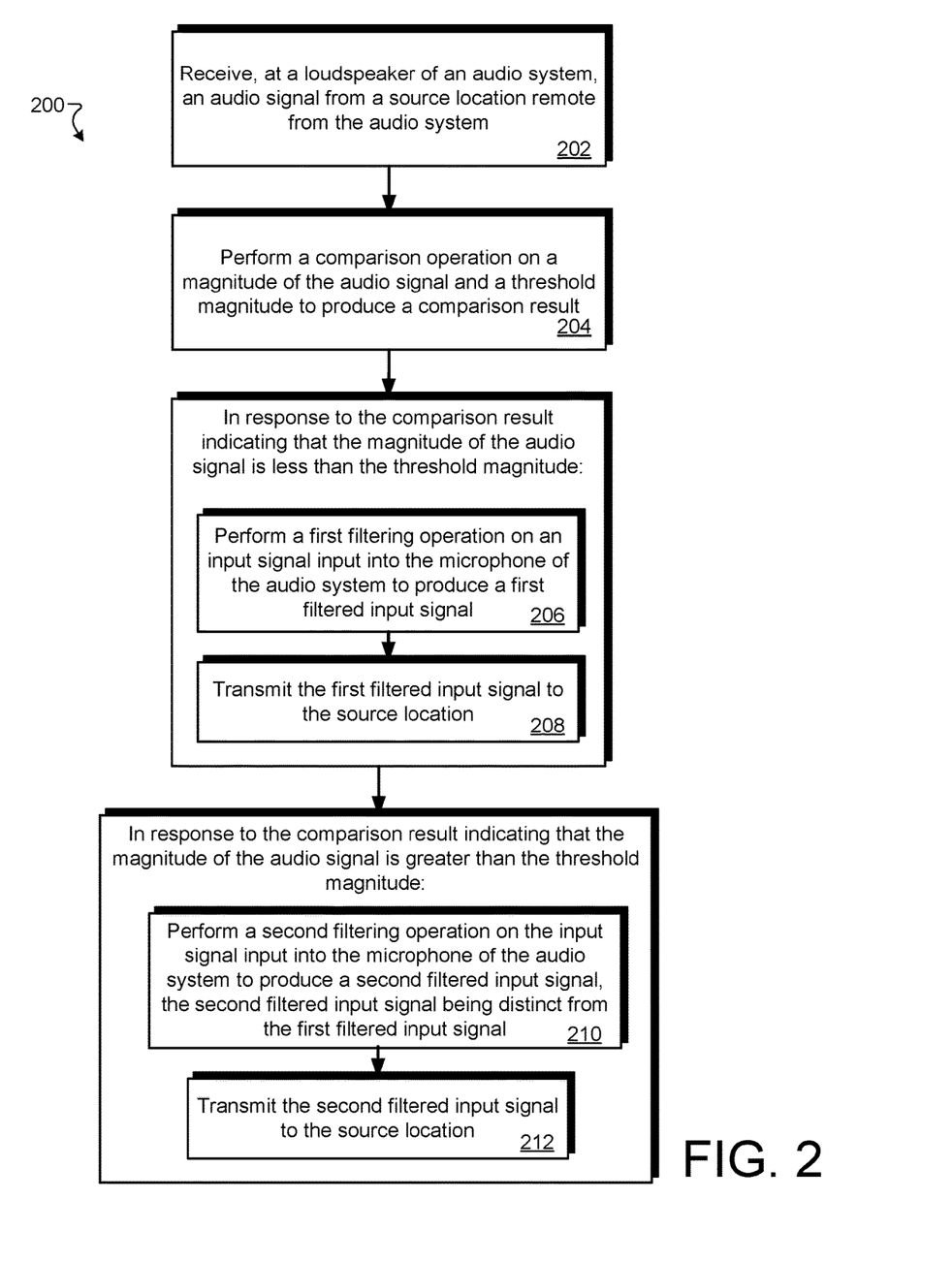
FIG. 2 is a flow chart that illustrates an example method of performing the improved techniques within the electronic environment shown in FIG. 1.

FIG. 2 is a flow chart that illustrates an example method 200 of performing echo cancellation. The method 200 may be performed by software constructs described in connection with FIG. 1, which reside in memory 126 of the mobile device 120 and are run by the set of processing units 124.

At 202, the mobile device 120 receives an audio signal from a source location remote from an audio system in which the mobile device 120 is configured to reduce acoustic echo. In some arrangements, e.g., that illustrated in FIG. 1, the audio system is included in the mobile device 120. In some arrangements, the audio signal is expressed as a discrete number of evenly-spaced samples of the audio signal over a window of time.

At 204, the mobile device 120 performs a comparison operation on a magnitude of the audio signal and a threshold magnitude to produce a comparison result, e.g., comparison result 144. In some arrangements, the magnitude comparison manager 136 computes the magnitude of the audio signal according to the $L^\infty$_norm, e.g., the maximum absolute value of a sample over the window of time. In some arrangements, the magnitude comparison manager 136 computes the magnitude of the audio signal according to the $L^2$_norm, e.g., the sum of the squares of the absolute values of the samples over the window of time.

At 206, in response to the comparison result indicating that the magnitude of the audio signal is less than the threshold magnitude, the mobile device 120 performs a first filtering operation on an input signal input into the microphone of the audio system to produce a first filtered input signal. In some arrangements, the mobile device 120 engages the small-magnitude filtering manager 140 to perform a convolution operation on the windowed audio signal, e.g., audio signal data 132, and the small-magnitude impulse response data 142. In some arrangements, the first filtered input signal subsequently produced is a residual signal equal to the difference between the input signal and the output of the convolution operation. At 208, the mobile device 120 transmits the first filtered input signal to the source location.

At 210, in response to the comparison result indicating that the magnitude of the audio signal is greater than the threshold magnitude, the mobile device 120 performs a second filtering operation on the input signal input into the microphone of the audio system to produce a second filtered input signal. In some arrangements, the mobile device 120 engages the large-magnitude filtering manager 150 to perform a convolution operation on a nonlinear function of the windowed audio signal, e.g., audio signal data 132, and the large-magnitude impulse response data 152. In some arrangements, the second filtered input signal subsequently produced is a residual signal equal to the difference between the input signal and the output of the convolution operation. At 212, the mobile device 120 transmits the second filtered input signal to the source location.

Figure 3:
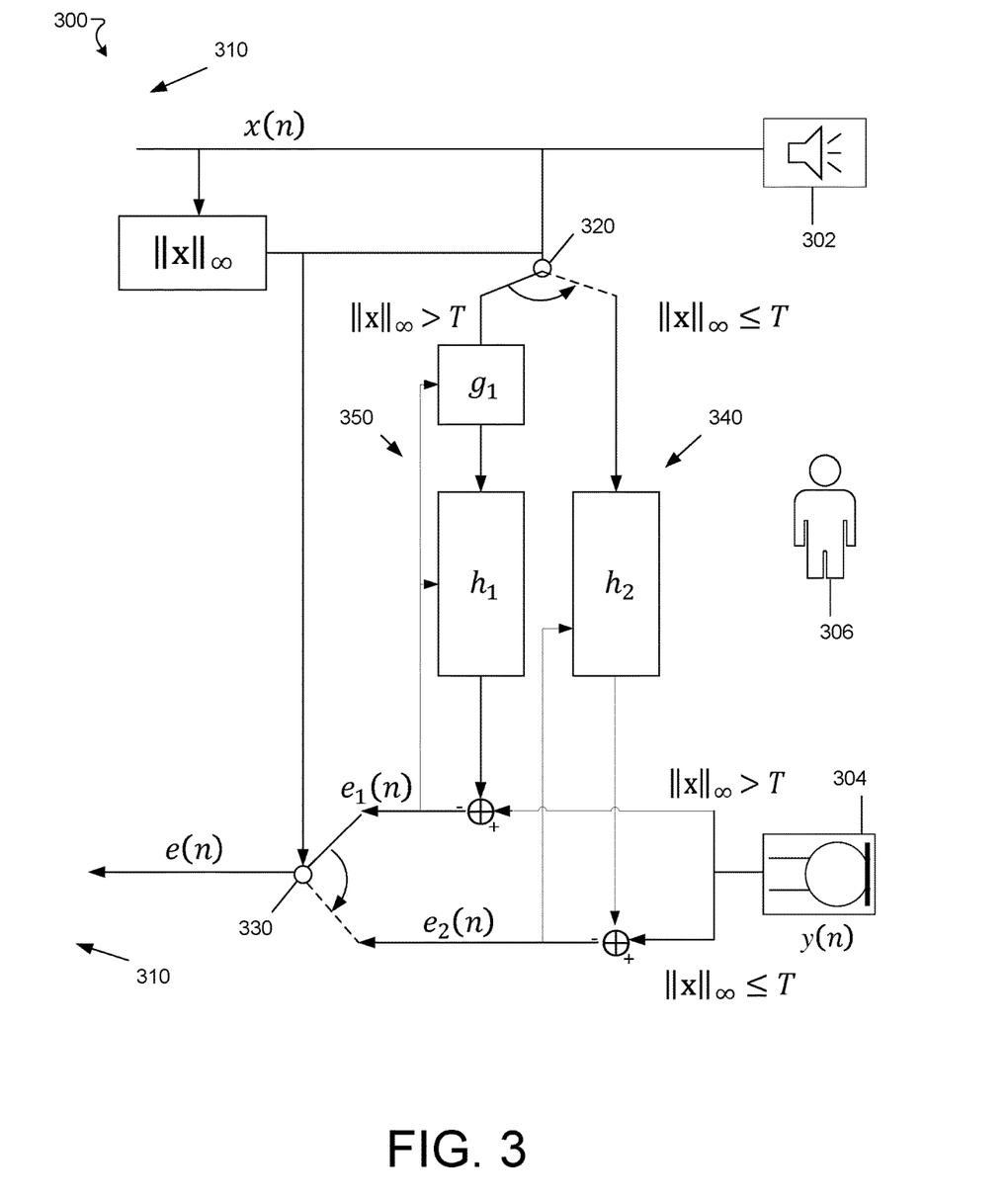
FIG. 3 is a schematic diagram that illustrates an example method of performing the improved techniques within the electronic environment shown in FIG. 1.

FIG. 3 is a schematic diagram illustrating an example audio system 300. As illustrated in this diagram, a sample of an audio signal x(n) arrives in the audio system 300 from a remote location 310 at an instant of time. Circuitry within the audio system 300 directs the audio signal x(n) to a loudspeaker 302 of the audio system 300, which is heard by a user 306.

Acoustic echo occurs when output from the loudspeaker 302 is picked up by the microphone 304 in addition to voice input from the user 306 to form an input signal y(n). Circuitry in the audio system 300 is configured to provide an output signal e(n) back to the remote location 310, that resembles what the user has provided to the microphone 306 and filters out the output from the loudspeaker 302.

Because of the inherent nonlinearity of the acoustic echo (e.g., due to proximity and quality of loudspeaker 302 and microphone 306 in a mobile device, e.g., mobile device 120), circuitry in the audio system 300 is configured to perform a filtering operation that depends upon a magnitude of the incoming audio signal x(n). As shown in FIG. 3 the audio system 300 computes a magnitude of the incoming audio signal x(n) according to the $L^\infty$ norm, i.e., $$\|x\|_\infty = \max_i \{|x(i)|\}_{i=1}^n,$$

where x(i) is the ith sample of the audio signal within a time window of n samples.

Once the magnitude of the incoming audio signal $\|x\|_\infty$ has been generated at some instant of time soon after the windowed signal x(n) has been received, the audio system 300 compares this magnitude with a threshold T at a switch 320. The audio system 300 then performs a filtering operation according to one of a small-magnitude branch 340 of the circuitry when $\|x\|_\infty < T$ and a large-magnitude branch 350 when $\|x\|_\infty > T$.

The small-magnitude branch 340 involves performing a linear filtering operation. This linear filtering operation involves subtracting a convolution between the windowed audio signal x(n) and an impulse response function $h_2(n)$ from the input signal y(n) to form a residual signal $e_2(n)$. For example, this residual signal might have the mathematical form $$e_2(n) = y(n) - \sum_{i=1}^n x(i) h_2(n+1-i).$$

The large-magnitude filtering operation 350 involves performing a nonlinear filtering operation. This nonlinear filtering operation involves subtracting a convolution between a nonlinear function $g_1$ of the windowed audio signal, i.e., $g_1[x(n)]$ and an impulse response function $h_1(n)$ from the input signal y(n) to form a residual signal $e_1(n)$. In some implementations, the nonlinear function may take the form $g_1(z)=z^2$. For example, this residual signal might have the mathematical form $$e_1(n) = y(n) - \sum_{i=1}^n g_1[x(i)] h_2(n+1-i).$$

The audio system 300 derives each of the impulse response functions $h_1(n)$ and $h_2(n)$ by minimizing a power of the respective residual signals $e_1(n)$ and $e_2(n)$. For example, the audio system may perform such a minimization for the residual signal $e_2(n)$ by finding the numbers $c_1, c_2, \ldots, c_n$ such that the residual signal power P, given by the expression $$P_2 = \sum_{j=1}^n \left| y(j) - \sum_{i=1}^j c_i x(i) \right|^2$$

is a minimum. In some implementations, the impulse response function takes the form of a weighted harmonic sum, i.e., a sum of coefficients times harmonics (e.g., a sine or cosine term), each harmonic having a frequency that is a multiple of a fundamental frequency. In such implementations, the circuitry of the audio system 200 may then apply standard techniques of Fourier analysis to generate the unknown weights.

Similarly, the expression for the power in the large-amplitude branch 350 is $$P_1 = \sum_{j=1}^n \left| y(j) - \sum_{i=1}^j c_i g_1[x(i)] \right|^2.$$

In some implementations, the audio system 300 updates the impulse response functions $h_1$ and $h_2$ periodically, e.g., according to a fixed, specified period. In some implementations, the period is equal to the size of the window of time.

In some implementations, the small-magnitude branch 350 involves applying a nonlinear function $g_2$ to the windowed audio signal prior to convolution, where $g_2$ is distinct from $g_1$.

In some implementations, there may be more than two branches at the switch 320. In such cases, there would be more than one threshold, i.e., with k branches, there would be k-1 thresholds $T_1, T_2, \ldots, T_{k-1}$. Along these lines, if the magnitude is less than $T_1$, then the audio system would provide a first filter (i.e., first nonlinear function and first impulse response function) according to a first branch; if the magnitude is greater than $T_1$ and less than $T_2$, then the audio system would provide a second filter according to a second branch, and so on.

Figure 4:
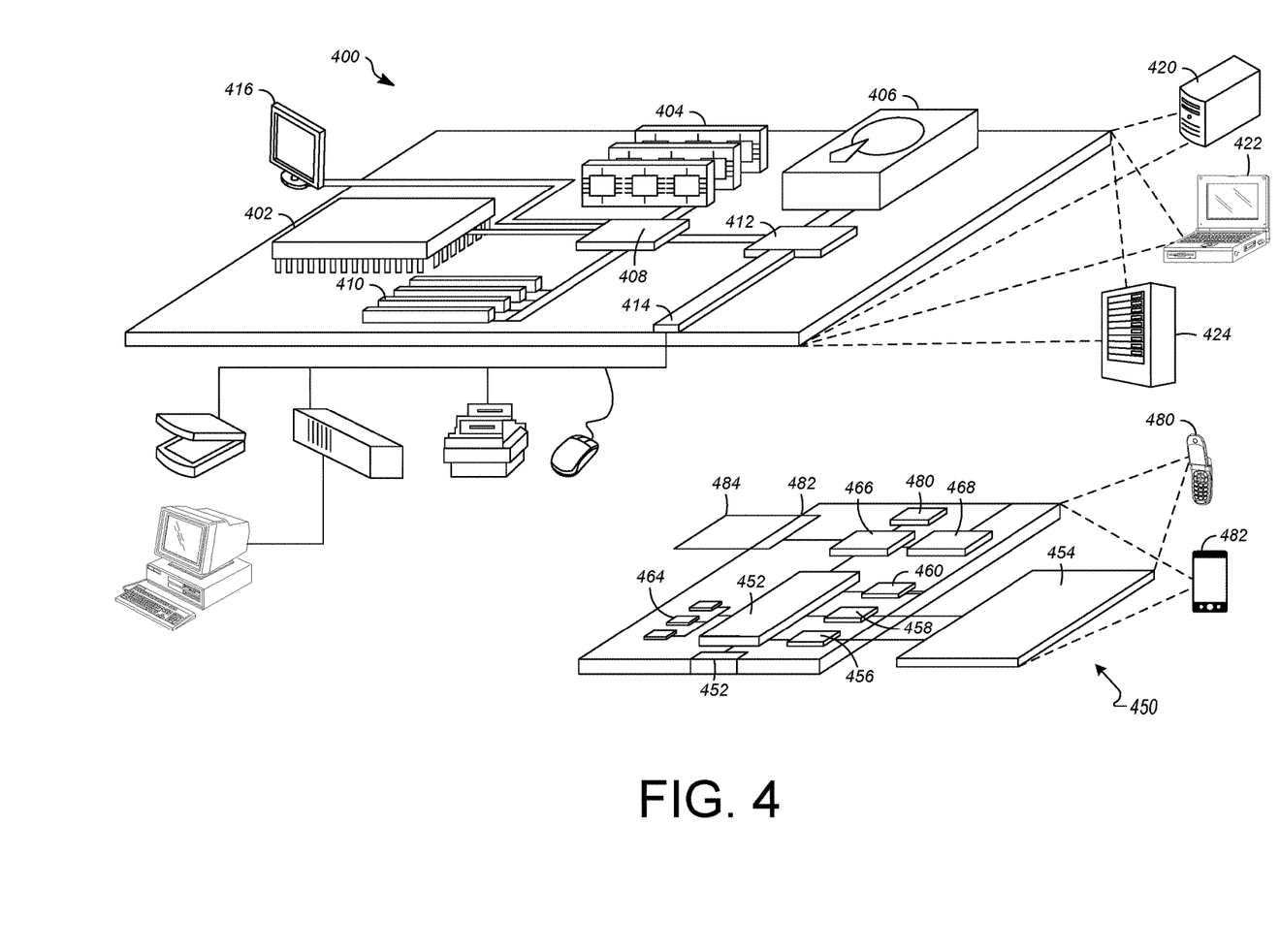
FIG. 4 illustrates an example of a computer device and a mobile computer device that can be used with circuits described here.

FIG. 4 illustrates an example of a generic computer device 400 and a generic mobile computer device 450, which may be used with the techniques described here.

As shown in FIG. 4, computing device 400 is intended to represent various forms of digital computers, such as laptops, desktops, workstations, personal digital assistants, servers, blade servers, mainframes, and other appropriate computers. Computing device 450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 400 includes a processor 402, memory 404, a storage device 406, a high-speed interface 408 connecting to memory 404 and high-speed expansion ports 410, and a low speed interface 412 connecting to low speed bus 414 and storage device 406. Each of the components 402, 404, 406, 408, 410, and 412, are interconnected using various busses, and may be mounted on a common motherboard or in other manners as appropriate. The processor 402 can process instructions for execution within the computing device 400, including instructions stored in the memory 404 or on the storage device 406 to display graphical information for a GUI on an external input/output device, such as display 416 coupled to high speed interface 408. In other implementations, multiple processors and/or multiple buses may be used, as appropriate, along with multiple memories and types of memory. Also, multiple computing devices 400 may be connected, with each device providing portions of the necessary operations (e.g., as a server bank, a group of blade servers, or a multi-processor system).

The memory 404 stores information within the computing device 400. In one implementation, the memory 404 is a volatile memory unit or units. In another implementation, the memory 404 is a non-volatile memory unit or units. The memory 404 may also be another form of computer-readable medium, such as a magnetic or optical disk.

The storage device 406 is capable of providing mass storage for the computing device 400. In one implementation, the storage device 406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 404, the storage device 406, or memory on processor 402.

The high speed controller 408 manages bandwidth-intensive operations for the computing device 400, while the low speed controller 412 manages lower bandwidth-intensive operations. Such allocation of functions is exemplary only. In one implementation, the high-speed controller 408 is coupled to memory 404, display 416 (e.g., through a graphics processor or accelerator), and to high-speed expansion ports 410, which may accept various expansion cards (not shown). In the implementation, low-speed controller 412 is coupled to storage device 406 and low-speed expansion port 414. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 420, or multiple times in a group of such servers. It may also be implemented as part of a rack server system 424. In addition, it may be implemented in a personal computer such as a laptop computer 422. Alternatively, components from computing device 400 may be combined with other components in a mobile device (not shown), such as device 450. Each of such devices may contain one or more of computing device 400, 450, and an entire system may be made up of multiple computing devices 400, 450 communicating with each other.

Computing device 450 includes a processor 452, memory 464, an input/output device such as a display 454, a communication interface 466, and a transceiver 468, among other components. The device 450 may also be provided with a storage device, such as a microdrive or other device, to provide additional storage. Each of the components 450, 452, 464, 454, 466, and 468, are interconnected using various buses, and several of the components may be mounted on a common motherboard or in other manners as appropriate.

The processor 452 can execute instructions within the computing device 450, including instructions stored in the memory 464. The processor may be implemented as a chipset of chips that include separate and multiple analog and digital processors. The processor may provide, for example, for coordination of the other components of the device 450, such as control of user interfaces, applications run by device 450, and wireless communication by device 450.

Processor 452 may communicate with a user through control interface 458 and display interface 456 coupled to a display 454. The display 454 may be, for example, a TFT LCD (Thin-Film-Transistor Liquid Crystal Display) or an OLED (Organic Light Emitting Diode) display, or other appropriate display technology. The display interface 456 may comprise appropriate circuitry for driving the display 454 to present graphical and other information to a user. The control interface 458 may receive commands from a user and convert them for submission to the processor 452. In addition, an external interface 462 may be provided in communication with processor 452, so as to enable near area communication of device 450 with other devices. External interface 462 may provide, for example, for wired communication in some implementations, or for wireless communication in other implementations, and multiple interfaces may also be used.

The memory 464 stores information within the computing device 450. The memory 464 can be implemented as one or more of a computer-readable medium or media, a volatile memory unit or units, or a non-volatile memory unit or units. Expansion memory 474 may also be provided and connected to device 450 through expansion interface 472, which may include, for example, a SIMM (Single In Line Memory Module) card interface. Such expansion memory 474 may provide extra storage space for device 450, or may also store applications or other information for device 450. Specifically, expansion memory 474 may include instructions to carry out or supplement the processes described above, and may include secure information also. Thus, for example, expansion memory 474 may be provided as a security module for device 450, and may be programmed with instructions that permit secure use of device 450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 464, expansion memory 474, or memory on processor 452, that may be received, for example, over transceiver 468 or external interface 462.

Device 450 may communicate wirelessly through communication interface 466, which may include digital signal processing circuitry where necessary. Communication interface 466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 468. In addition, short-range communication may occur, such as using a Bluetooth, WiFi, or other such transceiver (not shown). In addition, GPS (Global Positioning System) receiver module 470 may provide additional navigation- and location-related wireless data to device 450, which may be used as appropriate by applications running on device 450.

Device 450 may also communicate audibly using audio codec 460, which may receive spoken information from a user and convert it to usable digital information. Audio codec 460 may likewise generate audible sound for a user, such as through a speaker, e.g., in a handset of device 450. Such sound may include sound from voice telephone calls, may include recorded sound (e.g., voice messages, music files, etc.) and may also include sound generated by applications operating on device 450.

The computing device 450 may be implemented in a number of different forms, as shown in the figure. For example, it may be implemented as a cellular telephone 480. It may also be implemented as part of a smart phone 482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the specification.

It will also be understood that when an element is referred to as being on, connected to, electrically connected to, coupled to, or electrically coupled to another element, it may be directly on, connected or coupled to the other element, or one or more intervening elements may be present. In contrast, when an element is referred to as being directly on, directly connected to or directly coupled to another element, there are no intervening elements present. Although the terms directly on, directly connected to, or directly coupled to may not be used throughout the detailed description, elements that are shown as being directly on, directly connected or directly coupled can be referred to as such. The claims of the application may be amended to recite exemplary relationships described in the specification or shown in the figures.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

Further implementations are summarized in the following examples:

Example 1

A method, comprising: receiving, by processing circuitry configured to reduce acoustic echo in an audio system including a loudspeaker and a microphone, at the loudspeaker of the audio system, an audio signal from a source location remote from the audio system; performing, by the processing circuitry, a comparison operation on a magnitude of the audio signal and a threshold magnitude to produce a comparison result; in response to the comparison result indicating that the magnitude of the audio signal is less than the threshold magnitude: performing, by the processing circuitry, a first filtering operation on an input signal input into the microphone of the audio system to produce a first filtered input signal; and transmitting, by the processing circuitry, the first filtered input signal to the source location; in response to the comparison result indicating that the magnitude of the audio signal is greater than the threshold magnitude: performing, by the processing circuitry, a second filtering operation on the input signal input into the microphone of the audio system to produce a second filtered input signal, the second filtered input signal being distinct from the first filtered input signal; and transmitting, by the processing circuitry, the second filtered input signal to the source location.

Example 2

The method as in example 1, wherein performing the first filtering operation includes: sampling the audio signal over a specified window of time to produce a windowed audio signal; generating a first impulse response function based on the input signal input into the microphone; and generating a convolution of the windowed audio signal and the first impulse response function to produce a first filtered incoming signal.

Example 3

The method as in example 2, wherein generating the first impulse response function based on the input signal input into the microphone includes producing, as the first impulse response function, a generic impulse response function that optimizes a power of a residual signal, the residual signal being equal to a difference between the input signal input into the microphone and a convolution of the windowed audio signal and the generic impulse response function, and wherein transmitting the first filtered input signal to the source location includes sending, as the first filtered input signal, a power-optimized residual signal, the power-optimized residual signal being equal to the difference between the input signal input into the microphone and the convolution of the windowed audio signal and the first impulse response function.

Example 4

The method as in example 2 or 3, wherein the first impulse response function is a weighted sum of harmonics, each of the harmonics having a frequency equal to a multiple of a fundamental frequency.

Example 5

The method as in one of examples 2 to 4, wherein performing the first filtering operation further includes: after a specified amount of time after generating the first impulse response function, generating another, first impulse response function.

Example 6

The method as in one of examples 2 to 5, wherein the windowed audio signal includes a plurality of samples of the audio signal, each of the plurality of the samples being a value of the audio signal at a time that occurs within the specified window of time, and wherein performing the comparison operation on the magnitude of the audio signal and a threshold magnitude includes: generating an absolute value of each of the plurality of samples of the audio signal to produce a plurality of absolute values; and producing, as the magnitude of the audio signal, the largest of the plurality of absolute values.

Example 7

The method as in one of examples 1 to 6, wherein performing the second filtering operation includes: generating a nonlinear function of the windowed audio signal; generating a second impulse response function based on the input signal input into the microphone; and generating a convolution of i) the nonlinear function of the windowed audio signal and (ii) the first impulse response function to produce a first filtered incoming signal.

Example 8

The method as in example 7, wherein generating the nonlinear function of the windowed audio signal includes squaring the magnitude of the windowed audio signal.

Example 9

The method as in example 7 or 8, wherein generating the second impulse response function based on the input signal input into the microphone includes producing, as the second impulse response function, a generic impulse response function that optimizes a power of a residual signal, the residual signal being equal to a difference between the input signal input into the microphone and a convolution of the nonlinear function of the windowed audio signal and the generic impulse response function, and wherein transmitting the second filtered input signal to the source location includes sending, as the second filtered input signal, a power-optimized residual signal, the power-optimized residual signal being equal to the difference between the input signal input into the microphone and the convolution of the nonlinear function of the windowed audio signal and the second impulse response function.

Example 10

The method as in one of examples 6 to 9, wherein performing the second filtering operation further includes: after a specified amount of time after generating the second impulse response function, generating another, second impulse response function.

Example 11

A computer program product comprising a nontransitory storage medium, the computer program product including code that, when executed by processing circuitry configured to reduce acoustic echo in an audio system including a loudspeaker and a microphone, causes the processing circuitry to perform a method, the method comprising: receiving, at the loudspeaker of the audio system, an audio signal from a source location remote from the audio system; performing a comparison operation on a magnitude of the audio signal and a threshold magnitude to produce a comparison result; in response to the comparison result indicating that the magnitude of the audio signal is less than the threshold magnitude: performing a first filtering operation on an input signal input into the microphone of the audio system to produce a first filtered input signal; and transmitting the first filtered input signal to the source location; in response to the comparison result indicating that the magnitude of the audio signal is greater than the threshold magnitude: performing a second filtering operation on the input signal input into the microphone of the audio system to produce a second filtered input signal, the second filtered input signal being distinct from the first filtered input signal; and transmitting the second filtered input signal to the source location.

Example 12

The computer program product as in example 11, wherein performing the first filtering operation includes: sampling the audio signal over a specified window of time to produce a windowed audio signal; generating a first impulse response function based on the input signal input into the microphone; and generating a convolution of the windowed audio signal and the first impulse response function to produce a first filtered incoming signal.

Example 13

The computer program product as in example 12, wherein generating the first impulse response function based on the input signal input into the microphone includes producing, as the first impulse response function, a generic impulse response function that optimizes a power of a residual signal, the residual signal being equal to a difference between the input signal input into the microphone and a convolution of the windowed audio signal and the generic impulse response function, and wherein transmitting the first filtered input signal to the source location includes sending, as the first filtered input signal, a power-optimized residual signal, the power-optimized residual signal being equal to the difference between the input signal input into the microphone and the convolution of the windowed audio signal and the first impulse response function.

Example 14

The computer program product as in example 12 or 13, wherein performing the first filtering operation further includes: after a specified amount of time after generating the first impulse response function, generating another, first impulse response function.

Example 15

The computer program product as in one of examples 12 to 14, wherein the windowed audio signal includes a plurality of samples of the audio signal, each of the plurality of the samples being a value of the audio signal at a time that occurs within the specified window of time, and wherein performing the comparison operation on the magnitude of the audio signal and a threshold magnitude includes: generating an absolute value of each of the plurality of samples of the audio signal to produce a plurality of absolute values; and producing, as the magnitude of the audio signal, the largest of the plurality of absolute values.

Example 16

The computer program product as in one of examples 11 to 15, wherein performing the second filtering operation includes: generating a nonlinear function of the windowed audio signal; generating a second impulse response function based on the input signal input into the microphone; and generating a convolution of i) the nonlinear function of the windowed audio signal and (ii) the first impulse response function to produce a first filtered incoming signal.

Example 17

The computer program product as in example 16, wherein generating the nonlinear function of the windowed audio signal includes squaring the magnitude of the windowed audio signal.

Example 18

The computer program product as in example 16 or 17, wherein generating the second impulse response function based on the input signal input into the microphone includes producing, as the second impulse response function, a generic impulse response function that optimizes a power of a residual signal, the residual signal being equal to a difference between the input signal input into the microphone and a convolution of the nonlinear function of the windowed audio signal and the generic impulse response function, and wherein transmitting the second filtered input signal to the source location includes sending, as the second filtered input signal, a power-optimized residual signal, the power-optimized residual signal being equal to the difference between the input signal input into the microphone and the convolution of the nonlinear function of the windowed audio signal and the second impulse response function.

Example 19

The computer program product as in one of examples 16 to 18, wherein performing the second filtering operation further includes: after a specified amount of time after generating the second impulse response function, generating another, second impulse response function.

Example 20

An electronic apparatus configured to reduce acoustic echo in an audio system including a loudspeaker and a microphone, the electronic apparatus comprising: memory; and controlling circuitry coupled to the memory, the controlling circuitry being configured to: receive, at the loudspeaker of the audio system, an audio signal from a source location remote from the audio system; perform a comparison operation on a magnitude of the audio signal and a threshold magnitude to produce a comparison result; in response to the comparison result indicating that the magnitude of the audio signal is less than the threshold magnitude: perform a first filtering operation on an input signal input into the microphone of the audio system to produce a first filtered input signal; and transmit the first filtered input signal to the source location; in response to the comparison result indicating that the magnitude of the audio signal is greater than the threshold magnitude: perform a second filtering operation on the input signal input into the microphone of the audio system to produce a second filtered input signal, the second filtered input signal being distinct from the first filtered input signal; and transmit the second filtered input signal to the source location.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A method, comprising:
receiving, by processing circuitry configured to reduce acoustic echo in an audio system including a loudspeaker and a microphone, at the loudspeaker of the audio system, an audio signal from a source location remote from the audio system;
performing, by the processing circuitry, a comparison operation on a magnitude of the audio signal and a threshold magnitude to produce a comparison result;
in response to the comparison result indicating that the magnitude of the audio signal is less than the threshold magnitude:
performing, by the processing circuitry, a first filtering operation on an input signal into the microphone of the audio system to produce a first filtered input signal; and
transmitting, by the processing circuitry, the first filtered input signal to the source location;
in response to the comparison result indicating that the magnitude of the audio signal is greater than the threshold magnitude:
performing, by the processing circuitry, a second filtering operation on the input signal into the microphone of the audio system to produce a second filtered input signal, the second filtered input signal being different from the first filtered input signal; and
transmitting, by the processing circuitry, the second filtered input signal to the source location.

2. The method as in claim 1, wherein performing the first filtering operation includes:
sampling the audio signal over a specified window of time to produce a windowed audio signal;
generating a first impulse response function based on the input signal input into the microphone; and
generating a convolution of the windowed audio signal and the first impulse response function to produce a first filtered incoming signal.

3. The method as in claim 2, wherein generating the first impulse response function based on the input signal input into the microphone includes producing, as the first impulse response function, an impulse response function that optimizes a power of a residual signal, the residual signal being equal to a difference between the input signal input into the microphone and a convolution of the windowed audio signal and the generic impulse response function, and
wherein transmitting the first filtered input signal to the source location includes sending, as the first filtered input signal, a power-optimized residual signal, the power-optimized residual signal being equal to the difference between the input signal input into the microphone and the convolution of the windowed audio signal and the first impulse response function.

4. The method as in claim 2, wherein the first impulse response function is a weighted sum of harmonics, each of the harmonics having a frequency equal to a multiple of a fundamental frequency.

5. The method as in claim 2, wherein performing the first filtering operation further includes:
after a specified amount of time after generating the first impulse response function, generating another, first impulse response function.

6. The method as in claim 2,
wherein the windowed audio signal includes a plurality of samples of the audio signal, each of the plurality of the samples being a value of the audio signal at a time that occurs within the specified window of time, and
wherein performing the comparison operation on the magnitude of the audio signal and a threshold magnitude includes:
generating an absolute value of each of the plurality of samples of the audio signal to produce a plurality of absolute values; and
producing, as the magnitude of the audio signal, the largest of the plurality of absolute values.

7. The method as in claim 2, wherein performing the second filtering operation includes:
generating a nonlinear function of the windowed audio signal;
generating a second impulse response function based on the input signal input into the microphone; and
generating a convolution of (i) the nonlinear function of the windowed audio signal and (ii) the first impulse response function to produce a first filtered incoming signal.

8. The method as in claim 7, wherein generating the nonlinear function of the windowed audio signal includes squaring the magnitude of the windowed audio signal.

9. The method as in claim 7, wherein generating the second impulse response function based on the input signal input into the microphone includes producing, as the second impulse response function, a generic impulse response function that optimizes a power of a residual signal, the residual signal being equal to a difference between the input signal input into the microphone and a convolution of the nonlinear function of the windowed audio signal and the generic impulse response function, and
wherein transmitting the second filtered input signal to the source location includes sending, as the second filtered input signal, a power-optimized residual signal, the power-optimized residual signal being equal to the difference between the input signal input into the microphone and the convolution of the nonlinear function of the windowed audio signal and the second impulse response function.

10. The method as in claim 7, wherein performing the first filtering operation includes:
generating a first nonlinear function of the windowed audio signal, the first nonlinear function being different from the nonlinear function;
generating a first impulse response function based on the input signal input into the microphone; and
generating a convolution of (i) the first nonlinear function of the windowed audio signal and (ii) the first impulse response function to produce a first filtered incoming signal.

11. The method as in claim 6, wherein performing the second filtering operation further includes:

after a specified amount of time after generating the second impulse response function, generating another, third response function.

12. The method as in claim 1, wherein the method further comprises:
in response to the comparison result indicating that the magnitude of the audio signal is greater than the threshold magnitude and greater than a second threshold magnitude:
performing, by the processing circuitry, a third filtering operation on the input signal into the microphone of the audio system to produce a second filtered input signal, the third filtered input signal being different from the first filtered input signal and the second filtered input signal; and
transmitting, by the processing circuitry, the third filtered input signal to the source location.

13. A computer program product comprising a nontransitory storage medium, the computer program product including code that, when executed by processing circuitry configured to reduce acoustic echo in an audio system including a loudspeaker and a microphone, causes the processing circuitry to perform a method, the method comprising:
receiving, at the loudspeaker of the audio system, an audio signal from a source location remote from the audio system;
performing a comparison operation on a magnitude of the audio signal and a threshold magnitude to produce a comparison result;
in response to the comparison result indicating that the magnitude of the audio signal is less than the threshold magnitude:
performing a first filtering operation on an input signal into the microphone of the audio system to produce a first filtered input signal; and
transmitting the first filtered input signal to the source location;
in response to the comparison result indicating that the magnitude of the audio signal is greater than the threshold magnitude:
performing a second filtering operation on the input signal into the microphone of the audio system to produce a second filtered input signal, the second filtered input signal being different from the first filtered input signal; and
transmitting the second filtered input signal to the source location.

14. The computer program product as in claim 13, wherein performing the first filtering operation includes:
sampling the audio signal over a specified window of time to produce a windowed audio signal;
generating a first impulse response function based on the input signal input into the microphone; and
generating a convolution of the windowed audio signal and the first impulse response function to produce a first filtered incoming signal.

15. The computer program product as in claim 14, wherein generating the first impulse response function based on the input signal input into the microphone includes producing, as the first impulse response function, an impulse response function that optimizes a power of a residual signal, the residual signal being equal to a difference between the input signal input into the microphone and a convolution of the windowed audio signal and the generic impulse response function, and
wherein transmitting the first filtered input signal to the source location includes sending, as the first filtered input signal, a power-optimized residual signal, the power-optimized residual signal being equal to the difference between the input signal input into the microphone and the convolution of the windowed audio signal and the first impulse response function.

16. The computer program product as in claim 14, wherein the windowed audio signal includes a plurality of samples of the audio signal, each of the plurality of the samples being a value of the audio signal at a time that occurs within the specified window of time, and
wherein performing the comparison operation on the magnitude of the audio signal and a threshold magnitude includes:
generating an absolute value of each of the plurality of samples of the audio signal to produce a plurality of absolute values; and
producing, as the magnitude of the audio signal, the largest of the plurality of absolute values.

17. The computer program product as in claim 13, wherein performing the second filtering operation includes:
generating a nonlinear function of the windowed audio signal;
generating a second impulse response function based on the input signal input into the microphone; and
generating a convolution of (i) the nonlinear function of the windowed audio signal and (ii) the first impulse response function to produce a first filtered incoming signal.

18. The computer program product as in claim 17, wherein generating the second impulse response function based on the input signal input into the microphone includes producing, as the second impulse response function, a generic impulse response function that optimizes a power of a residual signal, the residual signal being equal to a difference between the input signal input into the microphone and a convolution of the nonlinear function of the windowed audio signal and the generic impulse response function, and
wherein transmitting the second filtered input signal to the source location includes sending, as the second filtered input signal, a power-optimized residual signal, the power-optimized residual signal being equal to the difference between the input signal input into the microphone and the convolution of the nonlinear function of the windowed audio signal and the second impulse response function.

19. The computer program product as in claim 17, wherein performing the second filtering operation further includes:
after a specified amount of time after generating the second impulse response function, generating another, third impulse response function.

20. An electronic apparatus configured to reduce acoustic echo in an audio system including a loudspeaker and a microphone, the electronic apparatus comprising:
memory; and
controlling circuitry coupled to the memory, the controlling circuitry being configured to:
receive, at the loudspeaker of the audio system, an audio signal from a source location remote from the audio system;
perform a comparison operation on a magnitude of the audio signal and a threshold magnitude to produce a comparison result;

in response to the comparison result indicating that the magnitude of the audio signal is less than the threshold magnitude:
  perform a first filtering operation on an input signal into the microphone of the audio system to produce a first filtered input signal; and
  transmit the first filtered input signal to the source location;

in response to the comparison result indicating that the magnitude of the audio signal is greater than the threshold magnitude:
  perform a second filtering operation on the input signal into the microphone of the audio system to produce a second filtered input signal, the second filtered input signal being different from the first filtered input signal; and
  transmit the second filtered input signal to the source location.

\* \* \* \* \*